United States Patent
Konishi et al.

(10) Patent No.: US 9,458,423 B2
(45) Date of Patent: Oct. 4, 2016

(54) CAPSULE FOR NON-FERROUS METAL COLLECTION AND METHOD FOR COLLECTING NON-FERROUS METAL

(71) Applicants: MORISHITA JINTAN CO., LTD., Osaka-shi, Osaka (JP); Yasuhiro Konishi, Sakai-shi, Osaka (JP)

(72) Inventors: Yasuhiro Konishi, Osaka (JP); Koshiro Tamaoki, Osaka (JP); Ryosei Kamaguchi, Osaka (JP); Daisuke Tagawa, Osaka (JP); Taku Hashimoto, Osaka (JP); Masaaki Nakatsuji, Osaka (JP)

(73) Assignees: MORISHITA JINTAN CO., LTD., Osaka (JP); Yasuhiro Konishi, Osaka (JP)

(*) Notice: Subject to any disclaimer, the term of this patent is extended or adjusted under 35 U.S.C. 154(b) by 0 days.

(21) Appl. No.: 14/603,882

(22) Filed: Jan. 23, 2015

(65) Prior Publication Data

US 2015/0130116 A1    May 14, 2015

Related U.S. Application Data

(63) Continuation of application No. 13/881,295, filed as application No. PCT/JP2011/075311 on Nov. 2, 2011, now abandoned.

(30) Foreign Application Priority Data

Nov. 2, 2010  (JP) ................................ 2010-246200

(51) Int. Cl.

| | |
|---|---|
| C22B 3/18 | (2006.01) |
| C12N 1/20 | (2006.01) |
| B01J 13/14 | (2006.01) |
| B01J 13/20 | (2006.01) |
| C22B 7/00 | (2006.01) |
| C22B 3/24 | (2006.01) |
| B29C 35/08 | (2006.01) |
| B29C 47/06 | (2006.01) |
| A61K 35/12 | (2015.01) |
| B29K 101/12 | (2006.01) |

(52) U.S. Cl.
CPC .................. *C12N 1/20* (2013.01); *B01J 13/14* (2013.01); *B01J 13/206* (2013.01); *B29C 35/0805* (2013.01); *B29C 47/065* (2013.01); *C22B 3/18* (2013.01); *C22B 3/24* (2013.01); *C22B 7/006* (2013.01); *A61K 2035/128* (2013.01); *B29C 2035/0827* (2013.01); *B29K 2101/12* (2013.01); *Y02P 10/234* (2015.11); *Y02P 10/238* (2015.11)

(58) Field of Classification Search
None
See application file for complete search history.

(56) References Cited

U.S. PATENT DOCUMENTS

| | | | |
|---|---|---|---|
| 4,769,223 A | 9/1988 | Volesky et al. | |
| 5,330,835 A | 7/1994 | Kikuchi et al. | |
| 5,348,803 A * | 9/1994 | Schlaemus | C02F 1/681 210/610 |
| 2004/0175412 A1 * | 9/2004 | Asada | A01H 4/00 424/439 |
| 2008/0009054 A1 | 1/2008 | Davor et al. | |
| 2011/0117622 A1 | 5/2011 | Yoshikado et al. | |

FOREIGN PATENT DOCUMENTS

| | | |
|---|---|---|
| JP | 2002-192178 | 7/2002 |
| JP | 2002-192186 | 7/2002 |
| JP | 2003-113427 | 4/2003 |
| JP | 2003-183477 | 7/2003 |
| JP | 2007-113116 | 5/2007 |
| JP | 2007-270250 | 10/2007 |
| JP | 2008-127604 | 6/2008 |
| JP | 2010-150569 | 7/2010 |
| WO | WO 2009/142170 | 11/2009 |
| WO | WO 2010/122545 | 10/2010 |

OTHER PUBLICATIONS

Extended European Search Report issued in counterpart European patent application (May 15, 2015).

* cited by examiner

*Primary Examiner* — Emily Cordas
(74) *Attorney, Agent, or Firm* — Hamre, Schumann, Mueller & Larson, P.C.

(57) ABSTRACT

Provided are: a capsule for non-ferrous metal collection that can collect a non-ferrous metal; and a method for collecting a non-ferrous metal using same. The capsule for non-ferrous metal collection comprises capsule contents and a covering section covering the capsule contents, and collects a non-ferrous metal within the capsule for non-ferrous metal collection by means of the capsule for non-ferrous metal collection being immersed in a solution containing a non-ferrous metal.

8 Claims, 6 Drawing Sheets

CAPSULE FOR NON-FERROUS METAL COLLECTION AND METHOD FOR COLLECTING NON-FERROUS METAL

This application is a Continuation of U.S. Ser. No 13/881,295, filed Jul. 3, 2013, which is a National Stage Application of PCT/JP2011/075311, filed Nov. 2, 2011, which applications are incorporated herein by reference.

TECHNICAL FIELD

The present invention relates to a capsule which can collect a non-ferrous metal, and a method of collecting a non-ferrous metal using the same.

BACKGROUND ART

Non-ferrous metals other than steel material (iron and alloy containing mainly iron) are becoming highly useful in industry; and an amount of a non-ferrous metal to be used is increasing. In order to avoid resource depletion of the non-ferrous metals, recycle technique which effectively utilizes non-ferrous metals contained in wastes such as home electric appliances is becoming highly important. For example, rare metal or rare noble metal is recovered from parts of wasted mobile phones, personal computers, automobiles and the like, which is sometimes called urban mines and intensely studied.

For recovering rare metal or rare noble metal, a recovery method using a chemical reaction, a recovery method using solvent extraction, and the like have been conventionally proposed. For example, JP-A 2010-150569 discloses a method for producing a platinum group element metal powder, comprising chlorinating waste material containing a platinum group element in a molten salt bath to form a metal chloride, and then subjecting the resulting metal chloride to reduction treatment to obtain metal powder having high purity. In the method, chlorine gas is blown into the molten salt bath and reacted at a temperature of 300 to 1000° C., whereby a chloride of a metal to be recovered is formed. Accordingly, a recovery method using a chemical reaction has a problem that consumption of a large amount of energy is accompanied. Further, there is also a problem that the cost of constructing a recovery system is necessary.

As the recovery method using solvent extraction, JP-A 2007-270250 discloses, as a method of selectively recovering a platinum group metal from an aqueous solution, a procedure of back-extracting palladium with an aqueous ammonia solution, and crystallizing palladium from the palladium-containing aqueous ammonia solution. The solvent extraction method has an advantage that, even when a concentration of a metal component is low, the metal component can be recovered. On the other hand, it is necessary to use a large amount of various solvents such as an organic solvent. For this reason, there is a problem that a large amount of waste solvent is generated and an environmental load is great.

JP-A 2008-127604 describes use of a biological membrane, such as an egg shell membrane, in a method of recovering a noble metal. The recovery method, however, needs an electric reduction recovery method, such as a gold electrolysis method, and has a different configuration from that of the method of the present invention.

OBJECT OF THE INVENTION

As a method of recovering a useful rare metal or rare noble metal, various methods have been studied as described above. However, the methods have some problems in respect of energy consumption or environmental load. As other methods, recovery methods using, for example, an adsorbent or a microorganism, are studied, but the methods also have a problem that a recovery rate is low. An object of the present invention is to solve such conventional problems.

SUMMARY OF THE INVENTION

That is, the present invention provides a capsule which can collect a non-ferrous metal easily and well, and a method of collecting a non-ferrous metal using the same.

The present invention provides a capsule for collecting a non-ferrous metal comprising a capsule content and a shell covering the capsule content, wherein the capsule is immersed in a solution containing the non-ferrous metal to collect the non-ferrous metal in the capsule, and the aforementioned problems are thus solved.

It is more preferable that the capsule content comprises one or more bacteria selected from the group consisting of *Geobacter* bacteria, *Desulfomonas* bacteria, *Desulfuromusa* bacteria, *Pelobacter* bacteria, *Shewanella* bacteria, *Ferrimonas* bacteria, *Aeromonas* bacteria, *Sulfurospirillum* bacteria, *Wolinella* bacteria, *Desulfovibrio* bacteria, *Geothrix* bacteria, *Deferribacter* bacteria, *Geovibrio* bacteria,*Pyrobaculum* bacteria, *Thermotogae* bacteria, *Archaeoglobus* bacteria, *Pyrococcus* bacteria and *Pyrodictium* bacteria.

In addition, it is more preferable that the capsule content comprises *Shewanella* bacteria.

In addition, it is more preferable that the capsule content comprises *Shewanella oneidensis* or *Shewanella algae*.

In addition, it is more preferable that the non-ferrous metal to be collected is one or more selected from the group consisting of a rare metal and a rare noble metal.

In addition, it is more preferable that the non-ferrous metal to be collected is palladium, platinum, rhodium, gold, silver, indium, gallium or a rare earth element.

It is more preferable that the capsule content further comprises at least one selected from the group consisting of an electron donating component, an electron accepting component and a liquid culture medium.

In addition, it is more preferable that the capsule for collecting a non-ferrous metal is a seamless capsule.

It is more preferable that the shell is obtained by curing a shell formation composition comprising a photocurable component and a shell permeation aid.

It is more preferable that the photocurable component is one or more selected from the group consisting of an acrylate-based oligomer, an unsaturated, polyester-based oligomer, a polyene thiol-based oligomer, a cinnamic acid-based oligomer, an epoxy-based oligomer, a vinyl ether-based oligomer and an unsaturated polyamide-based oligomer, and the shell permeation aid is one or more selected from the group consisting of alginic acid, polyvinyl alcohol, agar, carrageenan, gellan gum, pectin, starch, a starch derivative, dextrin, cellulose and protein.

Examples of one aspect of the capsule for collecting a non-ferrous metal include an aspect in which the capsule content comprises an oily portion containing *Shewanella* bacteria. It is more preferable that this capsule for collecting a non-ferrous metal is obtained by extruding an oily composition comprising *Shewanella* bacteria from a first nozzle, and extruding a shell formation composition from a second nozzle simultaneously into a carrier fluid, wherein the first nozzle and the second nozzle are concentrically arranged with sequentially increased radiuses in which the first nozzle is present innermost and the second nozzle is present outermost, and then curing the shell formation composition with light irradiation.

Examples of another aspect of the capsule for collecting a non-ferrous metal include an aspect in which the capsule comprises an intermediate layer portion containing an oily substance, and a hydrophilic portion containing *Shewanella* bacteria, wherein the intermediate layer portion is in layer structure at the time of preparing a capsule. It is more preferable that the capsule for collecting a non-ferrous metal is obtained by extruding a hydropbilic composition comprising *Shewanella* bacteria from a first nozzle, extruding an oily composition from a second nozzle and extruding a shell formation composition from a third nozzle simultaneously into a carrier fluid, wherein the first nozzle, the third nozzle and the third nozzle are concentrically arranged with sequentially increased radiuses in which the first nozzle is present innermost and the second nozzle is present outermost, and then curing the shell formation composition with light irradiation.

Further, the present invention also provides a method of collecting a non-ferrous metal, including:

an immersion step of immersing the capsule for collecting a non-ferrous metal in a solution containing a non-ferrous metal, and a separation step of separating the capsule for collecting a non-ferrous metal immersed in the immersing step.

Herein, it is preferable that the non-ferrous metal to be collected is one or more selected from the group consisting of a rare metal and a rare noble metal. It is more preferable that the non-ferrous metal to be collected is palladium, platinum, rhodium, gold, silver, indium, gallium or a rare earth element.

ADVANTAGES OF THE INVENTION

The capsule for collecting a non-ferrous metal of the present invention has an advantage that a non-ferrous metal can be easily collected by a simple operation of immersion in a solution containing a non-ferrous metal for a given time. In the collection of a non-ferrous metal, a non-ferrous metal can be effectively concentrated and collected, even in the case where an amount of a non-ferrous metal contained is very small.

In collection of a non-ferrous metal using the capsule for collecting a non-ferrous metal of the present invention, a non-ferrous metal can be collected without accompanying consumption of a large amount of energy like a method using chemical reaction. There is also an advantage that a large amount of waste solvent is not accompanied like a solvent extraction method, and the load on the environment is small. Further, in the present invention, since a non-ferrous metal can be collected by a simple operation of immersing the capsule for collecting a non-ferrous metal in a solution for a given period, and, thereafter, taking out the capsule by a means such as filtration, there is an advantage that the collection can be simply implemented without accompanying the large cost of facility investment.

DETAILED DESCRIPTION OF THE INVENTION

Capsule for Collecting Non-ferrous Metal and Method for Manufacturing the Same

The capsule for collecting a non-ferrous metal of the present invention is composed of a capsule content, and a shell covering the capsule, content. The capsule for collecting a non-ferrous metal is characterized in that a non-ferrous metal can be collected into the capsule by a simple operation of immersing the capsule in a solution containing a non-ferrous metal. In the present description, it is intended that the term, "collection" also includes the meaning "recovery", and the term "collecting a non-ferrous metal" also includes "recovering a non-ferrous metal".

In the present description, the "non-ferrous metal" means a metal except for iron and an alloy containing mainly iron. Examples of the non-ferrous metal to be collected in the present invention include a rare metal and a rare noble metal.

Herein, the rare metal means a metal other than a base metal (also called common metal or major metal) such as iron, copper, zinc, and aluminum, which is a metal not belonging to a noble metal such as gold and silver being a non-ferrous metal utilized in industry. Specific examples of the rare metal include lithium, beryllium, titanium, vanadium, chromium, manganese, cobalt, nickel, gallium, germanium, selenium, rubidium, strontium, zirconium, niobium, molybdenum, indium, antimony tellurium, cesium, barium, hafnium, tantalum, tungsten, rhenium, thallium, bismuth and a rare earth element. Examples of the rare earth element include scandium, yttrium, lanthanum, cerium, praseodymium, neodymium, promethium, samarium, europium, gadolinium, terbium, dysprosium, holmium, erbium, thulium, ytterbium and lutetium. In addition, the rare metal includes palladium, platinum and the like, and, in the present description, it is intended that palladium and platinum are included in the rare noble metal.

The rare noble metal means a metal, particularly, having a small amount of deposit, and excellent in corrosion resistance, among metals of Group 8 to Group 11 in the periodic table of chemical elements. Examples of the rare noble metal include gold, silver, platinum, palladium, rhodium, iridium, ruthenium and osmium.

More preferable examples of the metal to be collected by the capsule for collecting a non-ferrous metal of the present invention include palladium, platinum, rhodium, gold, silver, indium, gallium or a rare earth element.

The capsule for collecting a non-ferrous metal of the present invention is constructed of a capsule content and a shell covering the capsule content. Each constituent will be described below.

Capsule Content

It is preferable that the capsule content constituting the capsule for collecting a non-ferrous metal of the present invention contains bacteria selected from the following group:

*Geobacter* bacteria (representative species: *Geobacter metallireducens*: ATCC (American Type Culture Collection) 53774 strain),

*Desulfuromonas* bacterial (representative species: *Desulfuromonas palmitatis*: ATCC 51701 strain),

*Desulfuromusa* bacteria (representative species: *Desulfuromusa kysingii: Desulfuromusa kysingii* DSM. (Deutsche Sammlung von Mikroorganismen und Zellkulturen) 7343 strain),

*Pelobacter* bacteria (representative species: *Pelobacter venetianus*: ATCC 2394 strain),

*Shewanella* bacteria (*Shewanella* algae: ATCC 51181 strain, *Shewanella oneidensis*: etc),

*Ferrimonas* bacteria (*Ferrimonas balearica*: DSM 9799 strain),

*Aeromonas* bacteria (*Aeromonas hydrophila*: ATCC 15467 strain),

*Sulfurospirillum* bacteria (representative species: *Sulfurospirillum barnesii*: ATCC 700032 strain),

*Wolinella* bacteria (representative species: *Wolinella succinogenes*: ATCC 29543 strain),

*Desulfovibrio* bacteria (representative species: *Desulfovibrio desulfuricans*: ATCC 29577 strain),

*Geothrix* bacteria (representative species: *Geothrix fermentans*: ATCC 700665 strain),

*Deferribacter* bacteria (representative species: *Deferribacter thermophilus*: DSM 14813 strain),

*Geovibrio* bacteria (representative species: *Geovibrio ferrireducens*: ATCC 51996 strain),

*Pyrobaculum* bacteria (representative species: *Pyrobaculum islandicum*: DSM 4184 strain),

*Thermotogae* bacteria (representative species: *Thermotogae maritima*: DSM3109 strain),

*Archaeoglobus* bacteria (representative species: *Archaeoglobus fulgidus*: ATCC49558 strain),

*Pyrococcus* bacteria (representative species: *Pyrococcus furiosus* ATCC 43587 strain), and

*Pyrodictium* bacteria (representative species: *Pyrodictium abyssi*: DSM6158 strain).

Since the bacteria are contained in the capsule content of the capsule for collecting a non-ferrous metal, a non-ferrous metal can be collected in the capsule well.

In the present invention, it is preferable that the capsule content contains *Shewanella* bacteria. Examples of *Shewanella* bacteria include *Shewanella algae, Shewanella oneidensis, Shewanella algidipiscicola, Shewanella amazonensis, Shewanella baltica, Shewanella benthica, Shewanella colwelliana, Shewanella denitrifcans, Shewanella fidelis, Shewanella frigidimarina, Shewanella gelidimarina, Shewanella glacialipiscicola, Shewanella hafniensis, Shewanella hanedai, Shewanella japonica, Shewanella loihica, Shewanella marinintestina, Shewanella morhuae, Shewanella pealeana, Shewanella putrefaciens, Shewanella* sp. (KMM 3587) and *Shewanella woodyi*. It is more preferable that, among them, *Shewanella algae* or *Shewanella oneidensis* is contained in the capsule.

The bacteria may preferably be contained in the capsule for collecting a non-ferrous metal in the live state, or may be contained in the capsule for collecting a non-ferrous metal in the state of dead bacterial cells. For example, *Shewanella algae* and *Shewanella oneidensis* are characterized in that, even in the state of dead bacterial cells, a non-ferrous metal can be collected well.

In the present invention, the capsule content preferably contains the bacteria in an amount of 0.01 to 30 parts by mass, more preferably in an amount of 0.1 to 20 parts by mass, based on 100 parts by mass of the capsule content. For example, the bacteria is preferably contained at a ratio of 1 cell/capsule to $5 \times 10^{11}$ cells/capsule, more preferably at a ratio of $1 \times 10^3$ cells/capsule to $1 \times 10^{11}$ cells/capsule, based on the capsule content (based on one capsule).

In the capsule for collecting a non-ferrous metal of the present invention, the bacterium may be contained in the capsule content in the state of being dispersed in a hydrophilic composition such as an aqueous solution, or may be contained in the capsule content in the state of being dispersed in an oily composition.

Examples of the hydrophilic composition which can be used for preparing the capsule content include various aqueous solutions. Examples of the oily composition which can be used for preparing the capsule content include olive oil, jojoba oil, corn oil, rapeseed oil, lard, beef tallow, whale oil, castor oil soybean oil, rice oil, rice germ oil, coconut oil, palm oil, cacao oil, avocado oil, macadamia nut oil, squalane, mink oil, turtle oil, corn oil, hydrocarbons having 8 to 30 carbon atoms, beeswax, carnauba wax, rice wax, lanolin, liquid, paraffin, vaseline, fatty acids having 4 to 30 carbon atoms, esters of fatty acids having 4 to 30 carbon atoms and sucrose, esters of fatty acids having 4 to 30 carbon atoms and glycerol, aliphatic alcohols having 4 to 30 carbon atoms, esters of fatty acids having 4 to 30 carbon atoms and aliphatic alcohols having 4 to 30 carbon atoms, and silicone oil. These are employed solely or can be used in combination thereof. Among the oily compositions, liquid fat or oil having a viscosity of 200 mPA·s or lower in a temperature range of −30° C. to 60° C. is preferred.

The capsule content may further contain an additional component which can keep bacteria good, as necessary. Examples of the additional component are an electron donating component, an electron accepting component and various liquid media. When the bacteria are contained in the capsule content in the state of being dispersed in a hydrophilic composition, the following electron donating component or the like may preferably be contained in the capsule content.

The electron donating component in the present description means a component having a nature of donating an electron to the bacteria. The bacteria can grow well when the capsule content comprises both the electron donating component and the electron accepting component, because the two components are led to an oxidation-reduction reaction and the bacteria can get growth energy therefrom.

Examples of the electron donating component include:

a carboxylic acid having 1 to 7 carbon atoms and a derivative thereof, for example, formic acid, acetic acid, propionic acid, butyric acid, valeric acid, lactic acid, citric add, malic acid, tartaric acid, oxalic acid, malonic acid, succinic acid, glutaric acid, adipic acid, fumaric acid, maleic acid, and a salt thereof;

an aromatic carboxylic acid having 5 to 10 carbon atoms and a derivative thereof, for example, benzoic acid, phthalic acid, isophthalic acid, terephthalic acid, salicylic acid, gallic acid, mellitic acid, cinnamic acid, and a salt thereof;

an alcohol having 1 to 10 carbon atoms, for example, methanol and ethanol;

an unsaturated aromatic compound, for example, toluenephenol; and hydrogen gas.

Examples of the electron accepting component include a metal ion such as Fe (III) ion.

According to the present invention, the electron donating component can be suitably selected based on the type of bacteria to be used. For example, when *Shewanella algae* is used, a carboxylic acid having 1 to 7 carbon atoms or a derivative thereof, such as formic acid and lactic acid or a salt thereof can b preferably used as the electron donating component. If necessary as the electron accepting component, Fe (III) ion may also be used. By using the electron accepting component, growth energy derived from an oxidation-reduction reaction in cells can be obtained well.

When *Shewanella oneidensis* is employed, the electron donating component can preferably be a carboxylic acid having 1 to 7 carbon atoms or a derivative thereof (such as formic acid or a salt thereof).

In case where the bacteria are dispersed in an aqueous composition, it is necessary that oily substance may intervene as an intermediate layer portion between an aqueous composition containing the bacteria and a shell formation composition, when producing the capsule. The oily substance can be the same with those explained for the oily composition above. Preferable examples of the oily substance which can intervene as the intermediate layer portion include those having a melting point of 60° C. or lower (e.g., olive oil, jojoba oil, corn oil, rapeseed oil, lard, beef tallow, whale oil, castor oil, soybean oil, rice oil, rice germ oil, coconut oil, palm oil, cacao oil, avocado oil, macadamia nut oil, squalane, mink oil, turtle oil, and corn oil), and sucrose acetate isobutyrate (SAIB) and the like.

When the oily substance intervenes as the intermediate layer portion, the intermediate layer is preferably formed at a weight ratio of 5 to 40 parts by mass, and is more preferably formed at a weight ratio of 10 to 30 parts by mass, based on 100 parts by mass of the capsule for collecting a non-ferrous metal.

Shell

In the shell constituting the capsule for collecting a non-ferrous metal of the present invention, a component which can cover the capsule content well can be used without particular limitation. In the present invention, it is more preferable that the shell is formed from a shell formation composition containing a photocurable component. By forming the shell using the shell formation composition containing a photocurable component, there is an advantage that a capsule, particularly, a seamless capsule can be manufactured better and mere simply.

The photocurable component which can be used in the present invention is not limited as far as it is cured by light irradiation. In the present invention, it is more preferable to use an aqueous (hydrophilic) photocurable component as the photocurable component. By forming the shell using the aqueous (hydrophilic) photocurable component, the resulting capsule is excellent in water hydrophilicity of a capsule surface and shows excellent non-ferrous metal collecting property when it is immersed in an aqueous solution containing a non-ferrous metal. Examples of the photocurable component include a photopolymerizable oligomer and an addition polymerization product thereof. These may be used alone, or two or more of them may be used in combination.

Examples of the photopolymerizable oligomers are an acrylate-based oligomer, an unsaturated polyester-based oligomer, a polyene thiol-based oligomer, a cinnamic acid-based oligomer, an epoxy-based oligomer, a vinyl ether-based oligomer, and an unsaturated polyamide-based oligomer. More specifically an acrylate-based oligomer having at least two ethylene unsaturated bonds and a hydrophilic group in one molecule, a high acid value unsaturated polyester-based oligomer, a high acid value unsaturated epoxy-based oligomer, an anionic unsaturated acrylic oligomer, an unsaturated polyamide-based oligomer, and the like are suitably used. Among them, an acrylate-based oligomer having at least two ethylene unsaturated bonds and a hydrophilic group in one molecule is preferably used.

Examples of the acrylate-based oligomer having at least two ethylene unsaturated bonds and a hydrophilic group in one molecule include an oligomer having a photopolymerizable ethylene unsaturated group on both terminals of polyalkylene glycol. Examples of the acrylate-based oligomer include:

(1) polyethylene glycol di(meth)acrylates in which both terminal hydroxy groups of polyethylene glycol having a molecular weight of 400 to 6,000 are esterified with 2 moles of (meth)acrylic acid;

(2) polypropylene glycol di(meth)acrylates in which both terminal hydroxy groups of polypropylene glycol having a molecular weight of 200 to 4,000 are esterified with 2 moles of (meth)acrylic acid;

(3) an unsaturated polyethylene glycol urethanated product in which both terminal hydroxy groups of 1 mole of polyethylene glycol having a molecular weight of 400 to 6,000 are urethanated with 2 moles of a diisocyanate compound (tolylene diisocyanate, xylylene diisocyanate, isophorone diisocyanate, or the like) and, further, 2 moles of an unsaturated monohydroxy compound (2-hydroxyethyl (meth)acrylate, 2-hydroxypropyl (meth)acrylate, 3-hydroxypropyl (meth)acrylate, 4-hydroxybutyl (meth)acrylate, trimethylolpropane di(meth)acrylate, pentaerythritol tri (meth)acrylate, or the like) is added; and (4) an unsaturated polypropylene glycol urethanated product in which both terminal hydroxy groups of 1 mole of polypropylene glycol having a molecular weight of 200 to 40,000 are urethanated with 2 moles of a diisocyanate compound and, further, 2 moles of an unsaturated monohydroxy compound is added.

Examples of the high acid value unsaturated polyester-based oligomer include salts of an unsaturated polyester having an acid value of 40 to 200, obtained by esterifying polyvalent carboxylic acid having an unsaturated bond, and a polyhydric alcohol.

Examples of the high acid value unsaturated epoxy-based oligomer include an unsaturated epoxy oligomer having an acid value of 40 to 200. The oligomer is obtained, for examples, by preparing an addition reaction product of an epoxy compound and an unsaturated carboxyl compound ((meth)acrylic acid or the like), and adding an acid anhydride to a hydroxyl group remaining in the addition reaction product.

Examples of the anionic unsaturated acryl oligomer include an oligomer which is derived from at least two (meth)acryl-based monomers of (meth)acrylic acid and (meth)acrylic acid esters, and in which a photopolymerizabie ethylenic unsaturated group is introduced into a copolymer having a carboxyl group, a phosphoric acid group and/or a sulfonic acid group.

The unsaturated polyamide-based oligomer is obtained, for example, by adding an addition product of diisocyanate (tolylene diisocyanate, xylylene diisocyanate, or the like) and an ethylenic unsaturated hydroxy compound (2-hydroxyethyl acrylate or the like) to a water-soluble polyamide such as gelatin.

A number average molecular weight of the photopolymerizable oligomers is preferably 300 to 30,000, and more preferably 500 to 20,000. Herein, the number average molecule weight can be measured by a GPC (Gel Permeation Chromatography) method.

Among the photocurable components, an acrylate-based oligomer having a polymerizable ethylenic unsaturated group on both terminals of polyalkylene glycol can be particularly preferably used.

As the acrylate-based oligomer, commercially available products may be used. Examples of the acrylate-based oligomer which can be used in the present invention include an acrylate-based oligomer which is sold from Sanyu Rec Co., Ltd. under a trade name such as RM-6572, RM-6560, RM-6550, RM-6551, and RL-6527; an acrylate-based oligomer which is sold from Kansai Paint Co., Ltd. under a trade name such as ENT-1000, ENT-2000, ENT-3400, ENT-4000, ENTG-2000, and ENTG-3800; and an acrylate-based oligomer which is sold from Shin Nakamura Chemical Co., Ltd. under a trade name such as UA-7100, UA-7000, and UA-W2A.

The photocurable component is preferably contained as a solid content in the shell formation composition in an amount of 10 to 99% by mass, more preferably 20 to 90% by mass, and further preferably 40 to 90% by mass.

In the present invention, the shell is preferably formed from a composition containing the photocurable component, that is, a shell formation composition. The shell formation composition may further contain an additive such as a polymerization initiator, a photosensitizer, a coloring agent, a polymerizable monomer, a shell permeation aid, and an electric charge adjusting agent, as necessary. An amount of the additive is preferably 30% by mass or less, and more preferably 20% by mass or less, based on the mass of the shell formation composition, as a solid content.

As the polymerization initiator, a conventionally known polymerization initiator suitable for the photocurable component to be used can be used without particular limitation. As the polymerization initiator, a photopolymerization initiator is suitably used. The photopolymerization. initiator means a compound which can generate a polymerization initiation species by light irradiation and promote a polymerization reaction or a cross linking reaction. Examples of the photopolymerization initiator include benzoin, acetoin, benzoin methyl ether, benzoin ethyl ether, benzoin isopropyl ether, benzoin isobutyl ether, benzophenone, benzyl Michler's ketone, xanthone, chlorothioxanthone, isopropylthioxanthone, benzyl dimethyl ketal, naphthol, anthraquinone, hydroxyanthracene, acetophenone diethyl ketal, α-hydroxycyclohexyl phenyl ketone. 2-hydroxy-2-methylphenylpropane, an aromatic iodonium salt, an aromatic sulfonium salt, an iodonium salt, a sulfonium salt, a triarylsulfonium salt, a trifluorocarbon sulfonium salt and the like. The polymerization initiator may be used alone, or may be used by combining two or more kinds. The polymerization initiator is preferably contained in an amount of 0.001 to 20% by mass, more preferably 0.1 to 10% by mass, based on the mass of the shell formation composition, as a solid content. When an amount of the polymerization initiator is less than 0.001% by mass, there is a possibility of a problem that a polymerization reaction does not completely progress, a film strength cannot be provided, or the like and, when an amount exceeds 20% by mass, an initiation reaction excessively progresses, there is a possibility of a problem that a polymerization reaction does not progress, leading to decrease in a film strength, or the like. In the present invention, it is preferable that the photocurable component and the polymerization initiator, particularly the photopolymerization initiator are used by appropriately combining them.

When the shell is formed by curing the photocurable component with a visible light region, it is desirable that a photosensitizer is blended with the shell formation composition. Examples of the photosensitizer include a ruthenium complex and a porphyrin-based compound. The use amount of the photosensitizer is preferably 0.001 to 5% by mass, and more preferably 0.01 to 1% by mass, based on the mass of the shell formation composition, as a solid content.

If necessary, to the shell formation composition may be added a water-soluble monomer which is dissolved in an aqueous solvent at 80° C. or lower and has an unsaturated bond (e.g., itaconic acid, N,N'-methylenebisacrylate, hydroxyethyl methacrylate, hydroxypropyl methacrylate, N,N'-methylenebisacrylamide, N-isopropylacrylamide, N-vinylpyrrolidone, acryloylmorpholine, N,N'-dimethylacrylamide, and N-vinylformamide) alone or by combining two or more kinds. By using the water-soluble monomer, a reaction adversely influencing on a polymerization reaction can be suppressed, and strength of the shell can be further enhanced. An amount of the water-soluble monomer is preferably 0.01 to 30% by mass, and more preferably 0.1 to 25% by mass, based on the mass of the shell formation composition, as a solid content.

It is more preferable that the shell formation composition contains a shell permeation aid. A shell obtained by curing the shell formation composition containing a photocurable component and a shell permeation aid has an advantage that permeability of a non-ferrous metal ion is high and, therefore a non-ferrous metal can be collected better. Examples of the shell permeation, aid include alginic acid, polyvinyl alcohol, agar, carrageenan, gellan gum, pectin, starch, a starch derivative (alkylated starch, etherized starch, and the like), dextrin, cellulose, and protein. The shell permeation aid is preferably contained at a solid content ratio of 1 to 0.1 to 30% by mass, and more preferably 0.5 to 30% by mass, based on the shell formation composition.

When the shell permeation aid is contained in the shell formation composition, the shell formation composition is cured and then subjected to a treatment, such as enzyme treatment, alkali treatment or acid treatment for enhancing permeability of the shell. The treatments cut, degrade or dissolve a part of a polymer forming the shell, thereby making it possible to improve permeability of the shell.

As another aspect, the shell constituting the capsule for collecting a non-ferrous metal of the present invention can also be formed using the shell formation composition containing a thermosetting component. The thermosetting component can generally be used by a person skilled in the art. Examples of the thermosetting component include an acrylated-based oligomer, an unsaturated polyester-based oligomer, a polyene thiol-based oligomer, a cinnamic acid-based oligomer, an epoxy-based oligomer, a vinyl, ether-based oligomer, and an unsaturated polyamide-based oligomer, exemplified as the photopolymerizable oligomer.

When the shell is formed from the shell formation composition containing the thermosetting component, it is preferable that a thermal polymerization initiator is used together. The thermal polymerization initiator is generally used by a person skilled in the art. Specific examples of the thermal polymerization initiator include an azo compound such as 4,4'-azobis(4-cyanovaleric acid), 2,2'-azobis(2,4-dimethylvaleronitrile), 2,2'-azobis(isobutyronitrile), 2,2'-azobis(2-methylbutyranitrile), and dimethyl 2,2,-azobis(2-methylpropionate), and a peroxide compound such as dibenzoyl peroxide, tert-butyl hydroperoxide, cumene hydroperoxide, di-tert-butyl peroxide and the like. The thermal polymerization initiator is preferably contained in an amount of 0.001 to 20% by mass, and more preferably 0.1 to 10% by mass, based on the mass of the shell formation composition, as a solid content.

Also in the case where the shell is formed from the shell formation composition containing the thermosetting component, the aforementioned shell permeation aid can be used as described above.

In the capsule for collecting a non-ferrous metal in the present invention, the shell can also be formed from the shell formation composition containing a thermoplastic resin. Examples of the thermoplastic resin which can be used in formation of the shell include a thermoplastic resin which is generally used by a person skilled in the art, such as a polyolefin resin, for example, a polyethylene resin or a polypropylene resin, a polystyrene resin, an AS resin, an ABS resin, a vinyl chloride resin, an acrylic resin, a methacrylic resin, a methyl (meth)acrylate resin, a fluorine resin, a polycarbonate resin, or a polyester resin such as a polyethylene terephthalate resin or a polybutylene terephthalate resin. Also in the case where the shell is formed from the shell formation composition containing the thermoplastic resin, the aforementioned shell permeation aid can be used as described above.

The capsule for collecting a non-ferrous metal of the present invention encloses bacteria or the like therein. By immersing the capsule for collecting a non-ferrous metal in a solution containing a non-ferrous metal for a given time, the solution permeates through the shell, and enters the capsule. The bacteria are activated in the capsule, and non-ferrous metal collection activity is initiated. Thus, a non-ferrous metal is collected in the capsule. In the capsule for collecting a non-ferrous metal of the present invention, the bacteria are first activated by immersion in a solution containing a non-ferrous metal. For this reason, there is an advantage from the viewpoint of handling that a bacterium can be retained in the better state until immediately before immersion. There is also an advantage that damage of a bacterium at preservation of the capsule for collecting a non-ferrous metal can be reduced. In the case where the capsule for collecting a non-ferrous metal is a seamless capsule, there is an advantage that since the capsule has a spherical structure, an area of contact with a solution containing a non-ferrous metal is increased and, therefore, a non-ferrous metal can be collected better.

In collection of a non-ferrous metal using the capsule for collecting a non-ferrous metal of the present, invention, a non-ferrous metal can be collected without accompanying consumption of a large amount of energy like a method using a chemical reaction which is one kind of conventional methods. In addition, there is an advantage that a large amount of waste solvent is not accompanied and the load on environment is also small, in comparison with the conventional solvent extraction method which necessitates a large amount of solvent and gives heavy load on environment. In the present invention, there is another advantage that collection of the non-ferrous metal can be easily conducted without accompanying large cost of facility investment, because a non-ferrous metal can be collected by a simple operation of immersing the capsules for collecting a non-ferrous metal in a solution for a given period and the capsules are easily collected by a means such as filtration.

Method of Manufacturing Capsule for Collecting Non-Ferrous Metal

The capsule for collecting a non-ferrous metal of the present invention can be manufactured by extruding the shell formation composition and the capsule content into a carrier fluid, using a concentric double nozzle or a concentric triple nozzle, and then curing the shell formation composition with light irradiation.

In this manufacturing method, it is necessary that components which contact each other at preparation preferably have a different polarity from each other. For example, in a first embodiment shown in FIG. 1, it is preferred that the shell formation composition is hydrophilic and the capsule content is an oily composition containing *Shewanella* bacteria or the like.

Figure 1:
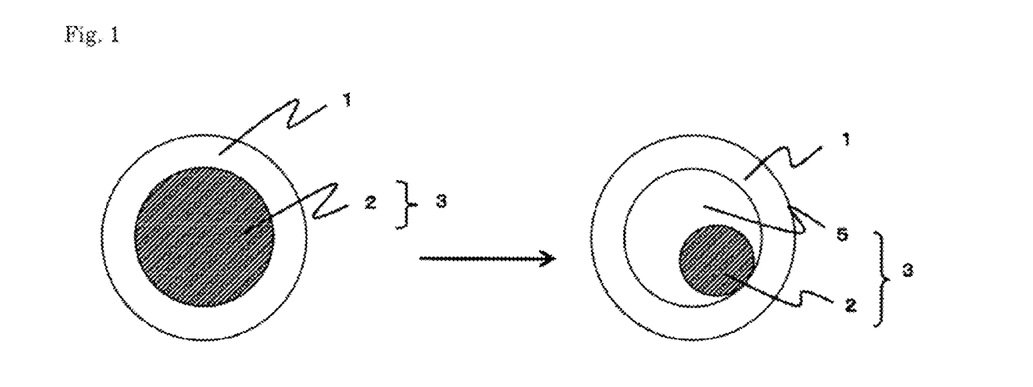
FIG. 1 is a schematic view showing one example of a preferable embodiment of the capsule for collecting a non-ferrous metal of the present invention, and is a schematic view showing a capsule for collecting a non-ferrous metal having a two-layered structure immediately after manufacturing.
Figure 2:
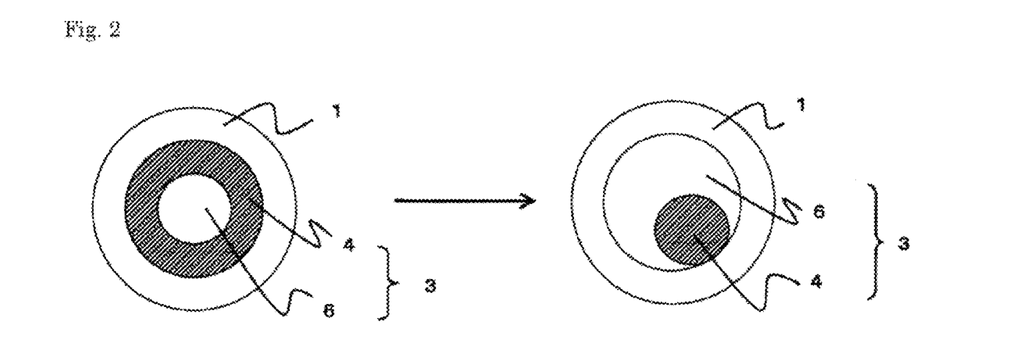
FIG. 2 is a schematic view showing another example of a preferable embodiment of the capsule for collecting a non-ferrous metal of the present invention, and is a schematic view showing a capsule for collecting a non-ferrous metal having a three-layered structure immediately after manufacturing.

FIGS. 1 and 2 show preferable embodiments of the capsule for collecting a non-ferrous metal of the present invention (first and second embodiments, respectively). With reference to the respective embodiment, the method of manufacturing the capsule for collecting a non-ferrous metal of the present invention will be described in detail.

Method of Manufacturing Capsule for Collecting Non-ferrous Metal Having Two-Layered Structure (First Embodiment)

Figure 3:
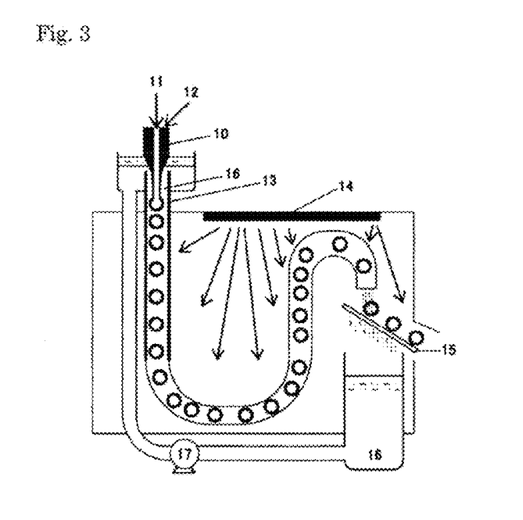
FIG. 3 is an outline view showing a method for manufacturing the capsule for collecting a non-ferrous metal of the present invention, having a two-layered structure, shown in FIG. 1.

A left drawing of FIG. 1 is a schematic view showing the capsule for collecting a non-ferrous metal having a two-layered structure immediately after manufacturing. The capsule for collecting a non-ferrous metal of the present invention having a two-layered structure shown in FIG. 1 (first embodiment) can be manufactured by an in-liquid dropwise addition method, for example, using a conventionally known capsule manufacturing apparatus provided with a concentric double nozzle (10) shown in FIG. 3. Specifically, as shown in FIG. 3, the capsule for collecting a non-ferrous metal having a two-layered structure can be manufactured by using a capsule manufacturing apparatus provided with a concentric double nozzle (10) having a first nozzle (internal side) and a second nozzle (external side) to extrude an oily composition containing bacteria (11) being the capsule content through the internal first nozzle, and a shell formation composition (12) through the external second nozzle into a carrier fluid (16) simultaneously, and then curing the shell formation composition with light irradiation.

In the method of manufacturing the capsule for collecting a non-ferrous metal of the first embodiment, the oily composition containing bacteria (11) being the capsule content is injected through the internal first nozzle, and the shell formation composition (12) is injected through the external second nozzle, via the concentric double nozzle (10). Then, upon contact between the capsule content and the shell formation composition in the carrier fluid (16), a seamless capsule of a two-layered structure is constructed due to a difference between polarity of the capsule content and polarity of the shell formation composition. More particularly, upon extrusion from the concentric double nozzle (1), a jet stream of a two-layered structure is formed due to interface tension present between the carrier fluid (16) and the shell formation composition (12). Then, the jet stream forms spherical liquid droplets having a two-layered structure by action of gravity. When forming liquid droplets, it is preferred that vibration is added to the jet stream to make a particle size of the liquid droplet to be uniform. The carrier fluid (16) is circulated in the apparatus desirably at a constant rate, by a driving means (17) such as a pump.

In addition, it is desirable that the carrier fluid (16) has different polarity from polarity of the shell formation composition. If the shell formation composition is hydrophilic (which is preferred), then the carrier fluid (16) would preferably be hydrophobic, i.e. oily substance. Examples of the carrier fluid include olive oil, jojoba oil, corn, oil, rapeseed oil, lard, beef tallow, whale oil, castor oil, soybean oil, rice oil, rice germ oil, coconut oil, palm oil, cacao oil, avocado oil, macadamia nut oil, squalane, mink oil, turtle oil, corn oil, hydrocarbons having 8 to 30 carbon atoms, beeswax, carnauba wax, rice wax, lanolin, liquid paraffin, vaseline, fatty acids having 4 to 30 carbon atoms, esters of fatty acids having 4 to 30 carbon atoms and sucrose, esters of fatty acids having 4 to 30 carbon atoms and glycerol, aliphatic alcohols having 4 to 30 carbon atoms, esters of fatty acids having 4 to 30 carbon atoms and aliphatic alcohols having 4 to 30 carbon atoms, silicone oil and the like. The carrier fluid may be used solely or in combination thereof. It is more preferred that the carrier fluid has a viscosity of 10 to 300 mPa·s, and more preferably 30 to 200 mPa·s in the temperature range of 0° C. to 30° C.

The spherical liquid droplets having a two-layered structure are then irradiated with light using a light source (14). The light irradiation may be performed at any stage and, for example, the light irradiation may be performed in the carrier fluid (16), or may be performed after separation of liquid droplets and the carrier fluid (16) via a separation means (15) such as a net. Thus, the capsule for collecting a non-ferrous metal having a two-layered structure shown in a left drawing of FIG. 1 can be obtained.

The light source (14) is not particularly limited, as far as it can radiate light having a wavelength of about 200 nm to about 800 nm and includes, for example, a mercury lamp, a fluorescent lamp, a xenon lamp, a carbon arc lamp, and a metal halide lamp. The light source can be appropriately selected depending on a photocurable component used. When a photosensitizer is blended with the shell formation composition, the photocurable component can be cured by visible light. An irradiation time can be set depending on an intensity of the light source or a distance from the light source. The irradiation time can generally be 0.05 seconds to 10 minutes, preferably 0.1 seconds to 2 minutes.

The shell formation composition is cured by light irradiation to form a shell, thus obtaining capsules for collecting a non-ferrous metal. The resulting capsules may be dried by a normal pressure drying method or a reduced pressure drying method as necessary.

In the first embodiment (FIG. 1), since polarity of the capsule content (2) and polarity of the shell formation composition forming the shell (1) are different from each other, a capsule for collecting a non-ferrous metal can be simply produced. There is also an advantage that a particle size distribution can be set narrow.

The obtained capsules of the present invention are immersed in a solution containing a non-ferrous metal, in which the solution containing a non-ferrous metal permeates the shell and enters into the capsules. A right drawing of FIG. 1 is a view showing the state where, after immersion, a solution containing a non-ferrous metal (5) permeates a capsule, and the solution is present in the interior of the capsule. The bacteria and the solution in the capsule are brought into contact with each other, and the bacteria are activated. Then, non-ferrous metal collection activity by the bacteria is initiated, and a non-ferrous metal is collected in the capsule.

The capsule for collecting a non-ferrous metal may be immersed in a liquid culture medium before immersion in a solution containing a non-ferrous metal, as necessary to culture bacteria in the capsule. For example, the capsules of the present invention are immersed in a liquid culture medium such as TSB (Trypticase Soy Broth) at a pH of about 7 and 30° C. for 6 to 72 hours, and number of bacterial in the capsules can be increased by culturing.

Method of Manufacturing Capsule for Collecting Non-ferrous Metal Having Three-Layered Structure (Second Embodiment)

A left drawing of FIG. 2 is a schematic view showing a capsule for collecting a non-ferrous metal having a three-layered structure immediately after manufacturing. The capsule for collecting a non-ferrous metal of the present invention having a three-layered structure (second embodiment) shown in this FIG. 2 can be manufactured, for example, by an in-liquid dropwise addition method, using a conventionally known capsule manufacturing apparatus, in which the concentric double nozzle is changed to a concentric triple nozzle, shown in FIG. 3. Specifically, the capsule for collecting a non-ferrous metal having a three-layered structure can be manufactured by using a capsule manufacturing apparatus provided with a concentric triple nozzle having a first nozzle (innermost portion), a second nozzle (intermediate portion) and a third nozzle (outermost portion) to extrude a hydrophilic composition containing *Shewanella* bacteria or the like through the first nozzle, an oily composition through the second nozzle, and a shell formation composition through the third nozzle into a carrier fluid (16) simultaneously, and then curing the shell formation composition with light irradiation. A specific procedure and the like in this method are the same as those described above, with the exception that a concentric triple nozzle is used in place of the concentric double nozzle.

In the capsule for collecting a non-ferrous metal obtained by the manufacturing method, an intermediate layer consisting of an oily substance (4) is present in the state of covering a hydrophilic composition (6) containing a bacterium of *Shewanella* bacteria or the like, immediately after manufacturing. The presence of the intermediate layer portion (4) makes it possible that the capsule content and the shell forming composition both have same polarity, for example, when the capsule content is hydrophilic composition (6) containing *Shewanella* bacteria or the like, and a shell formation composition (1) can be same polarity (hydrophilicity).

The obtained capsule having a three-layered structure may be brought into the state where the oily substance (4) is localized, as shown in a right drawing of FIG. 2, over time, by performing the aforementioned bacterium culturing treatment, or immersion in a solution containing a non-ferrous metal. Thereby the bacteria and the solution in the capsule are brought into contact with each other well, and the bacteria can be activated well. Then, non-ferrous metal collection activity by the bacteria is initiated, and a non-ferrous metal is collected into the capsule.

In the capsules having a three-layered structure, a composition obtained by concentrating bacteria in a hydrophilic substance can be used as the capsule content, as it is. Accordingly, the hydrophilic composition containing bacteria can be prepared more easily. In addition, since a hydrophilic composition can be used as the capsule content, there is also an advantage that an electron donating component and/or an electron accepting component can be contained in the capsule content well.

The capsule of the present invention has a particle size of preferably 0.1 to 10 mm, and more preferably 0.1 to 5 mm. The particle size of the capsule of the present invention can be appropriately selected depending on a kind and/or a concentration of a non-ferrous metal contained in a solution, a concentration of bacteria contained in the capsule, and the like.

When the shell is formed using the shell formation composition containing a thermosetting component, the capsule for collecting a non-ferrous metal can be manufactured by using a heated carrier fluid in place of using the light source which radiates light, in the aforementioned manufacturing method.

In the ease where the shell is formed from the shell formation composition containing a thermoplastic resin, the capsule for collecting a non-ferrous metal can be manufactured by using a cooled carrier fluid in place of using the light source which radiates light, in the aforementioned manufacturing method. In the case where the shell formation composition containing a thermoplastic resin is used, it is preferable that a heating means is provided in a nozzle portion in a capsule manufacturing apparatus.

Method of Collecting Non-ferrous Metal

According to the present invention, a non-ferrous metal can be collected using the capsule of the present invention. The method of collecting a non-ferrous metal in the present invention includes the following steps:

an immersion step of immersing the capsule for collecting a non-ferrous metal in a solution containing a non-ferrous metal, and a separation step of separating the capsule for collecting a non-ferrous metal immersed in the immersion step.

The solution containing a non-ferrous metal, which can be used in the method of the present invention, is not limited as far as it contains one or more of non-ferrous metals selected from the group consisting of a rare metal and a rare noble metal. Examples of the solution include a non-ferrous metal-containing aqueous solution (percolate) prepared from:

a sea bottom mineral resource, such as cobalt-rich crust, manganese crust, manganese nodule, and sea bottom hot water mineral deposit, a marine mineral resource, such as sea water, a land mineral resource, such as metal-containing oxidized mineral (e.g., laterite and monazite), a waste component-containing recycle resource, such as metal-containing incineration residue obtained upon incineration of waste, and urban mine, and the like.

It is preferable that the mineral component, such as a non-ferrous metal contained in the solutions is crushed or ground in advance. When the particle size of the mineral component is large, a specific surface area is small and thus a solid-liquid contact area is decreased, leading to deterioration in non-ferrous metal collection efficiency. In addition, when the particle size of the mineral component is larger as mentioned above, the mineral component is easily precipitated, and thus there is a possibility that trouble is generated in an operation of collecting a non-ferrous metal.

According to the method of the present invention, the capsule for collecting a non-ferrous metal is immersed in the solution containing a non-ferrous metal and a non-ferrous metal contained in the solution permeates the shell constituting the capsule. Thereby, a non-ferrous metal is collected in the capsule.

If necessary, an electron donating component and/or electron accepting component may be added to a solution containing a non-ferrous metal. By adding these components, an efficiency of collecting a non-ferrous metal may be enhanced. For example, the electron donating component can preferably be added to the solution containing a non-ferrous metal in a concentration of 1 to 500 mM.

If necessary the pH of the solution containing a non-ferrous metal may be adjusted. It is more preferable that the solution containing a non-ferrous metal has a pH in the range of 6 to 9.

An immersion time for immersing the capsule for collecting a non-ferrous metal in the solution containing a non-ferrous metal can be appropriately selected depending on a concentration of a non-ferrous metal in the solution, and the like. The immersion time can generally be 6 to 240 hours.

The capsules in which non-ferrous metal is collected by the immersion are separated from the solution. The separation operation herein has an advantage that the capsule for collecting a non-ferrous metal can be separated by a very simple operation, for example, filtration or sieving. The collected metal can be easily taken out by performing treatment of destructing a capsule structure, or incineration treatment of a capsule component under a temperature in such a range that does not adversely influence on the collected metal.

The capsule for collecting a non-ferrous metal of the present invention has an advantage that a non-ferrous metal can be easily collected by a simple operation of immersion in the solution containing a non-ferrous metal for a given time. In this collection of a non-ferrous metal, there is an advantage that, even in the case where an amount of a non-ferrous metal contained is small, a non-ferrous metal can be concentrated and collected effectively.

EXAMPLES

The present invention will be described in more detail by way of the following Examples, but the present invention is not limited to them. In Examples, unless otherwise indicated, "part" and "%" are on a mass basis.

Example 1

Example 1 is a capsule for collecting a non-ferrous metal having a two-layered structure immediately after manufacturing, in which a capsule content is an oily portion containing *Shewanella* bacteria, and a shell covering the capsule content is obtained by curing a shell formation composition containing a hydrophilic photocurable component.

The shell formation composition was prepared by mixing 60 parts by mass of a 40% aqueous solution of ENTG-3800 (manufactured by Kansai Paint Co., Ltd.), 0.6 parts by mass of acetoin, and 20 parts by mass of a 0.5% aqueous poval solution.

The capsule content was prepared by dispersing and suspending *Shewanella oneidensis* being reducing bacteria cultured at a high concentration in coconut oil being an oily substance, to prepare a suspension composition in which a concentration was adjusted to $1.2 \times 10^8$ cells/capsule per one capsule.

Then, the capsules were obtained using an apparatus having a concentric double nozzle (a seamless capsule manufacturing apparatus, manufactured by Morishita Jintan Co., Ltd.), shown in FIG. 3, in which the suspension composition was injected through an internal nozzle of a double nozzle, and the shell formation composition was injected through an external nozzle simultaneously into a carrier fluid flowing down to form capsule particles in the carrier fluid. Ultraviolet ray was radiated using a high pressure mercury lamp of a wavelength of 320 to 400 nm immediately after formation of the capsule particles to polymerize the photocurable component (ENTG-3800) of the shell formation composition, to obtain seamless capsules of a two-layered structure having a particle size of 4 mm. Liquid paraffin was used as the carrier fluid.

Example 2

Example 2 is a capsule for collecting a non-ferrous metal having a three-layered structure immediately after manufacturing, in which a capsule content is a hydrophilic portion containing *Shewanella* bacteria, a shell covering the capsule content is obtained by curing a shell formation composition containing a hydrophilic photocurable component, and an intermediate layer is made of an oily substance.

The shell formation composition was prepared by mixing 60 parts by mass of a 40% aqueous solution of ENTG-3800 (manufactured by Kansai Paint Co., Ltd.), 0.6 parts by mass of acetoin, and 20 parts by mass of a 0.5% aqueous poval solution.

The capsule content was prepared from a hydrophilic internal layer composition in which a concentration of *Shewanella oneidensis* being a reducing bacterium cultured at a high concentration was adjusted so that the bacterium was contained in a hydrophilic solution culture medium at $1.2 \times 10^8$ cells/capsule per one capsule.

The intermediate layer was prepared from an oily composition obtained by mixing sucrose acetate isobutyrate (SAIB) and coconut oil at a mass ratio of 50:50.

Then, the capsules were obtained using an apparatus in which a concentric doable nozzle was replaced with a concentric triple nozzle (a seamless capsule manufacturing apparatus, manufactured by Morishita Jintan Co., Ltd.) instead of the apparatus having the concentric double nozzle shown in FIG. 3, in which the capsule content was injected through an innermost nozzle of a triple nozzle, the intermediate layer composition was injected through an middle nozzle, and the shell formation composition was injected through an outermost nozzle simultaneously into an oily fluid flowing down to form capsule particles in the oily fluid. Ultraviolet ray was radiated using a high pressure mercury lamp of a wavelength of 320 to 400 nm immediately after formation of capsule particles to polymerize a photocurable component (ENTG-3800) of the shell formation composition, to obtain seamless capsules for collecting a non-ferrous metal of a three-layered structure having a particle size of 4 mm. Silicone oil was used as a carrier fluid.

Example 3

The seamless capsules for collecting a non-ferrous metal of a two-layered structure obtained in Example 1 were immersed in a TSB liquid culture medium at a pH of 7.2 and 30° C. for 48 hours, and *Shewanella oneidensis* contained in the capsules was cultured.

The cultured capsules were washed using a buffer solution ($KH_2PO_4$/NaOH). Then, the capsules were immersed in an aqueous solution (25° C., pH 7.0) containing 1 mM Pd (II) ion and 50 mM formic acid. Number of the capsules immersed in the aqueous solution is $1.2 \times 10^7$ capsules/m³.

Pd(II) ion concentrations were measured by an ICP (Inductively Coupled Plasma) light emission analyzing device at times of 3 minutes, 1 hour, 2 hours, 3 hours, 4 hours, 5 hours and 24 hours passing after immersion of the capsules.

After 24 hours from the capsule immersion, the aqueous solution containing the capsule was filtered, and the immersed capsules were taken out.

In this experiment, the capsules were milky white after the culturing operation and before immersion operation. On the other hand, the capsules taken out after 24 hours from capsule immersion were gray to black.

As comparative tests without using capsules, the aqueous solution containing Pd (II) ion and formic acid obtained above was employed, without adding anything (Comparative Example 1: control). The aqueous solution containing Pd (II) ion and formic acid was mixed, with *Shewanella oneidensis* which was not encapsulated at a bacteria concentration of $6.7 \times 10^{15}$ cells/m³ to suspend the cells (Comparative Example 2). The aqueous solution containing Pd (II) ion and formic acid was mixed with *Shewanella oneidensis* not encapsulated at a bacteria concentration of $6.7 \times 10^{15}$ cells/m³ to suspend the cells and the concentration of formic acid was adjusted to 200 mM (Comparative Example 3). Pd (II) ion concentrations were measured at times of 3 minutes, 1 hour, 2 hours, 3 hours, 4 hours, 5 hours and 24 hours passing after the bacteria were put in, using an ICP light emission analyzing device.

Figure 4:
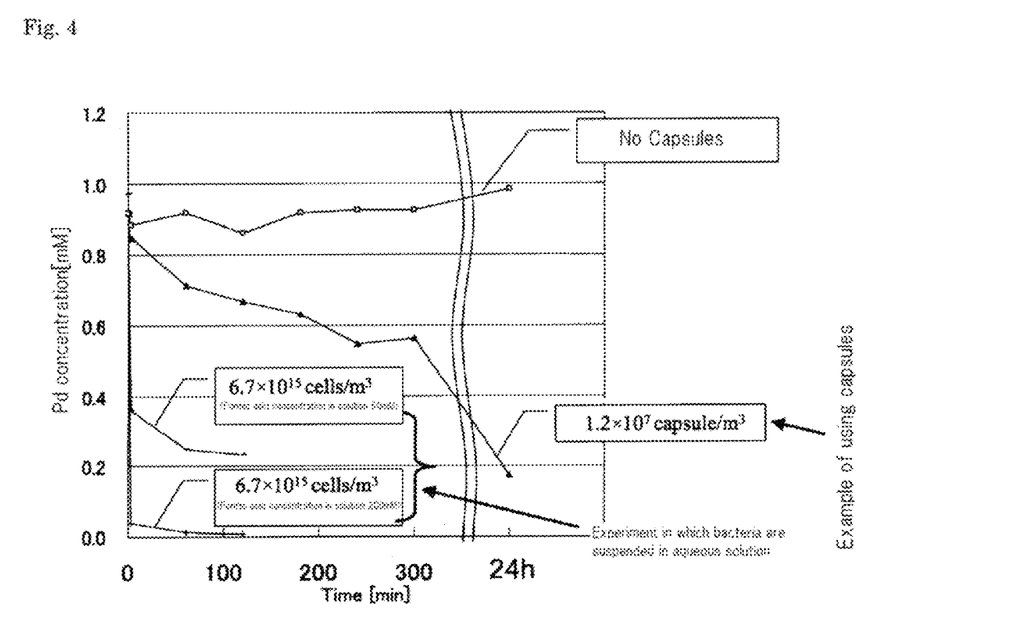
FIG. 4 is a graph chart showing changes in Pd (II) ion concentration in an aqueous solution in Example 3 and Reference Comparative Example.

A graph showing changes in Pd (II) ion concentration in the aqueous solution in Example 3 and these comparative tests is shown in FIG. 4.

In two comparative tests in which *Shewanella oneidensis* was added as it is to suspend the cells, measurement was stopped because Pd (II) ion concentration after 2 hours was considerably decreased.

Example 4

The seamless capsules for collecting a non-ferrous metal of a two-layered structure obtained in Example 1 were immersed in a TSB liquid culture medium at a pH of 7.2 and 30° C. for 48 hours, and *S. oneidensis* contained in the capsule was cultured.

The cultured capsules were washed with a buffer solution ($KH_2PO_4$/NaOH). Then, the capsules were immersed in an aqueous solution (25° C., pH 7.0) containing 5 mM Pd(II) ion and 200 mM formic acid. Number of capsules immersed in the aqueous solution was $1.2 \times 10^7$ capsules/m³.

After 24 hours from the capsule immersion, the aqueous solution containing the capsules was filtered, and the immersed capsules were taken out.

In this experiment, the capsules after the culturing operation and before immersion operation were milky white. On the other hand, the capsules taken out after 24 hours from capsule immersion were black.

Figure 5:
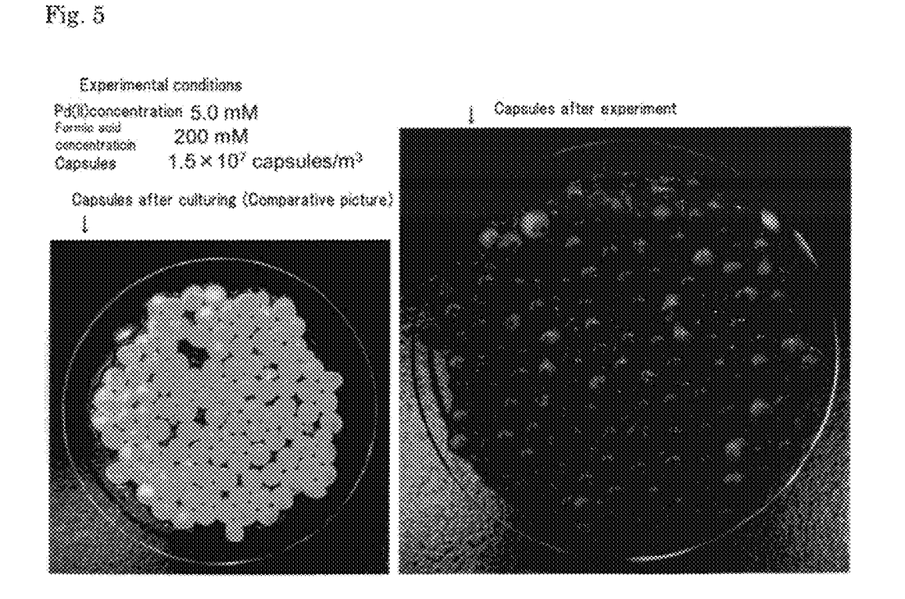
FIG. 5 shows photographs of the capsules for collecting a non-ferrous metal before a solution immersion operation (after culturing operation, before solution immersion) and the capsules for collecting a non-ferrous metal taken out after 24 hours from solution immersion, used in Example 4.

Photographs of the capsules before immersion operation (after culturing operation, before immersion experimental operation, left), and the capsules taken out after 24 hours from capsule immersion (right) are shown in FIG. 5.

As shown in Example 3, the concentration of a palladium ion in the aqueous solution could be significantly reduced by immersing the capsules for collecting a non-ferrous metal of the present invention in the aqueous solution containing a palladium ion for 24 hours. The capsules after immersion were gray to black, and the capsules could be easily taken out by filtration.

In the comparative test in which *Shewanella oneidensis* was added as it is to the aqueous solution containing a palladium ion at a concentration of $6.7 \times 10^{15}$ cells/m$^3$ to suspend the cells, palladium ion in the aqueous solution was significantly reduced at time of 2 hours. However, in this experimental example, it was difficult to take out the bacteria by filtration or the like, because *Shewanella oneidensis* was dispersed in the suspended state.

Example 5

The capsules for collecting a non-ferrous metal having a three-layered structure immediately after manufacturing obtained in Example 2 were immersed in a TSB liquid culture medium at a pH of 7.2 and 30 degrees for 48 hours as in Examples 3 and 4, and bacteria contained in the capsule were cultured.

The cultured capsules were washed using a buffer solution ($KH_2PO_4$/NaOH). Then, the resulting capsules were immersed in an aqueous solution (pH 3.5, 20 mL) having an indium chloride concentration of 1 mM. Number of the capsules which were immersed in the aqueous solution was 100. Number of bacteria present in the capsules immersed in the aqueous solution was $1.0 \times 10^{10}$ cells/ml.

The concentrations of an indium ion contained in the aqueous solution were measured using an ICP light emission analyzing device at a time before capsule immersion, and at times of 5 minutes, 30 minutes, 1 hour, 2 hours, 3 hours and 6 hours after capsule immersion. The collection rate of indium at the time after 6 hours from capsule immersion was 98.5%.

In addition, as a comparative test, also regarding the aqueous solution in which the capsule was not immersed, the indium ion concentration was measured at each of the aforementioned times.

Figure 6:
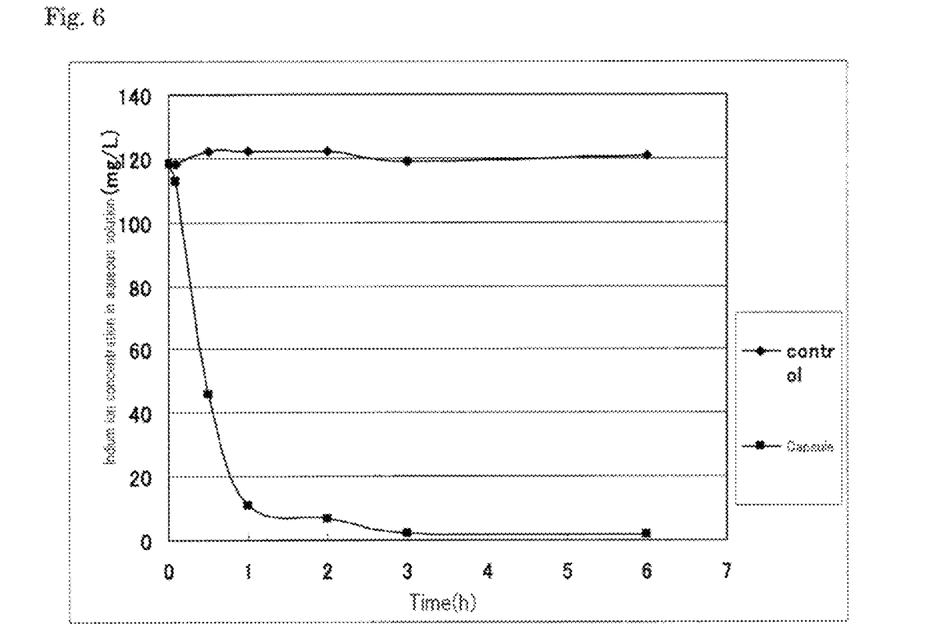
FIG. 6 is a graph chart showing changes in indium concentration in an aqueous solution in Example 5 and Comparative Test.

A graph showing changes in indium ion concentration in the aqueous solution in Example 5 and the comparative test is shown in FIG. 6.

Example 6

Example 6 shows that gold was recovered from wastes of IC chips. Capsules having a three-layered structure immediately after manufacturing were prepared as follow.

A shell formation composition was prepared by mixing 60 parts by mass of a 40% aqueous solution of RM-6572 (manufactured by Sanyu Rec Co., Ltd.), 0.6 parts by mass of acetoin, and 20 parts by mass of a 0.5% aqueous poval solution.

A hydrophilic internal layer composition was prepared as a capsule content by mixing *Shewanella algae* being a reducing bacterium cultured at a high concentration in a hydrophilic solution culture medium so that the bacteria was contained at $1.2 \times 10^8$ cells/capsule per one capsule.

An oily composition was prepared as an intermediate layer composition by mixing sucrose acetate isobutyrate (SAIB) and coconut oil at a mass ratio of 50:50.

Then, capsules were obtained using an apparatus in which a concentric double nozzle was replaced with a concentric triple nozzle (seamless capsule manufacturing apparatus, manufactured by Morishita Jintan Co., Ltd.) instead of the apparatus having a concentric double nozzle shown in FIG. 3, wherein the capsule content was injected through an innermost nozzle of a triple nozzle, the intermediate layer composition was injected through an intermediate nozzle, and the shell formation composition was injected through an outermost nozzle simultaneously into an oily fluid flowing down to form capsule particles in the oily fluid. Ultraviolet ray was radiated on the capsule particles using a high pressure mercury lamp of a wavelength of 320 to 400 nm immediately after formation of capsule particles to polymerize a photocurable component (RM-6572) of the shell formation composition, to obtain seamless capsules for collecting a non-ferrous metal of a three-layered structure having a particle size of 4 mm. Silicone oil was used as a carrier fluid.

The capsules for collecting a non-ferrous metal having a three-layered structure, thus obtained, were immersed in a TSB liquid culture medium at a pH of 7.2 and 30 degrees for 48 hours as in Examples 3 and 4, and the bacteria contained in the capsule were cultured.

The cultured capsules was washed using a buffer solution ($KH_2PO_4$/NaOH).

Wasted IC (semiconductor integrated circuit) chips were finely ground to obtain an IC chip ground product. The resulting IC chip ground product was immersed for 1 day in an aqueous solution, a pH of which had been adjusted to 0.7 using hydrochloric acid, to prepare an IC chip percolate.

The capsules obtained above were Immersed in the obtained IC chip percolate (pH 0.7, 20 mL). Number of the capsules that were immersed in the IC chip percolate was 100. Number of the bacteria present in the capsule immersed in the IC chip percolate was $3.0 \times 10^{10}$ cells/ml.

Concentrations of gold element contained in the IC chip percolate were measured using an ICP light emission analyzing device at a time before capsule immersion and at times of 10 minutes, 30 minutes, 1 hour, 2 hours, 3 hours and 6 hours after capsule immersion. A collection rate of gold after 6 hours from capsule immersion in Example 6 was 75.7%.

As comparative experiments without capsules, the IC chip percolate was employed as it is without bacteria. Separately, *Shewanella algae* was added to the IC chip percolate at a concentration of $4.0 \times 10^{10}$ cells/ml to suspend the cells. Concentration of gold ion was measured at each of the aforementioned times using an ICP light emission analyzing device.

Figure 7:
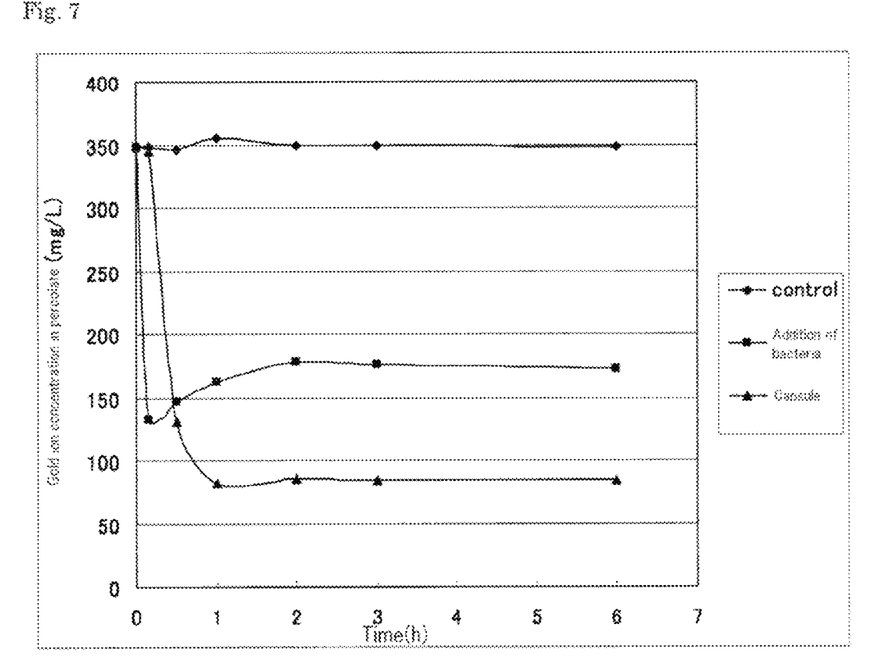
FIG. 7 is a graph chart showing changes in gold concentration in an IC chip percolate in Example 6 and Comparative Test.

A graph showing changes in concentration of gold ion ([$AuCl_4$]$^-$) in the IC chip percolate in Example 6 and the comparative tests is shown in FIG. 7.

From the Examples 5 and 6, it was confirmed that indium and gold could be collected using the capsules for collecting a non-ferrous metal of the present invention.

Further, as shown, in Example 6, it was also confirmed that gold could be recovered from the wasted IC chips. The IC chip percolate used in Example 6 is a strong acidic aqueous solution, having a pH of 0.7. It was confirmed that gold could be recovered well from the strong acidic aqueous solution.

In addition, also in the comparative test of Example 6, in which *Shewanella algae* was added as it is to the IC chip percolate at a concentration of $4.0 \times 10^{10}$ cells/ml to suspend the cells, concentration of gold ion was significantly reduced. However, in Example 6, it was difficult to take out the bacterial by filtration or the like, because *Shewanella algae* was dispersed as they were in the suspension state.

In addition, Example 6 shows that the capsules for collecting a non-ferrous metal of the present invention can selectively collect only gold, from an IC chip percolate although the IC chip percolate contains a variety of metal other than gold as collection subject metal. The IC chip percolate contains a variety of metal components such as copper other than gold. It was confirmed that the concentration of copper ion contained in the IC chip percolate used in Example 6 is as high as the concentration of gold ion. Nevertheless, a metal component collected in the capsules for collecting a non-ferrous metal was only gold in Example 6. Thus, it was confirmed that the capsules for collecting a non-ferrous metal of the present invention had extremely excellent performance that only gold could be selectively collected from the IC chip percolate containing gold and copper.

Example 7

The capsules for collecting a non-ferrous metal having a three-layered structure immediately after manufacturing, manufactured in Example 6, were subjected to the culturing operation as explained in Example 6.

The resulting capsules were immersed in an aqueous solution (pH 7.0, 20 mL) containing 1 mM platinum (IV) ion and 50 mM sodium lactate. Number of the capsules immersed in the aqueous solution was 100. Number of the bacteria present in the capsule immersed in the aqueous solution was $3.0 \times 10^{10}$ cells/ml.

Concentrations of platinum contained in an aqueous solution were measured using an ICP light emission spectral analysis device at a time before capsule immersion, and at times of 10 minutes, 30 minutes, 1 hour, 3 hours, and 6 hours after capsule immersion. A collection rate of platinum after 6 hours from capsule immersion in Example 7 was 72.0%.

In addition, as a comparative test, the aqueous solution was employed as it was without the capsules and a platinum concentration was measured at each of the aforementioned times.

Figure 8:
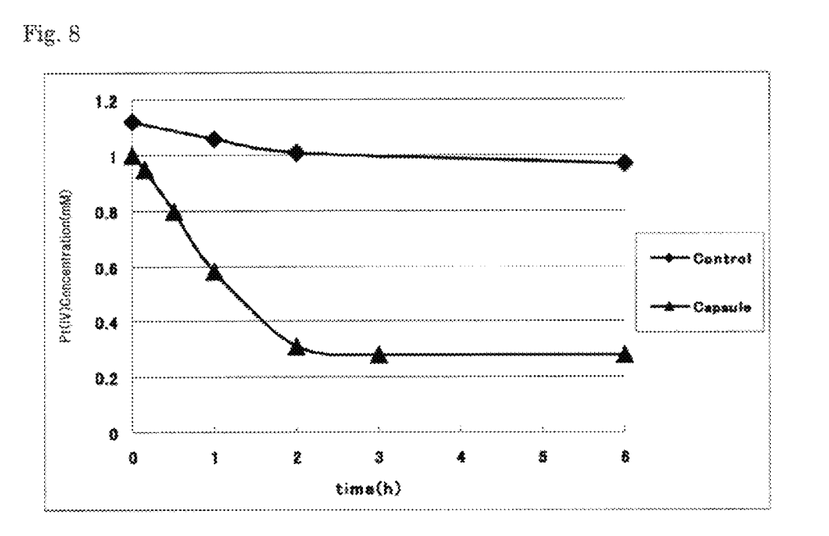
FIG. 8 is a graph chart showing changes in platinum (IV) concentration in an aqueous solution in Example 7 and Comparative Test.

A graph showing changes in platinum (IV) concentration in the aqueous solution in Example 7 and this comparative test is shown in FIG. 8.

Example 8

According to the same manner as that of Example 6 except that, as the shell formation composition forming a shell, a composition in which 60 parts by mass of a 40% aqueous solution of UA-7100 (manufactured by Shin-Nakamura Chemical Co., Ltd.), 0.6 parts by mass of acetoin, and 20 parts by mass of a 0.5% aqueous poval solution were mixed, was prepared and used, capsules for collecting a non-ferrous metal having a three-layered structure immediately after manufacturing was obtained. Then, the resulting capsules were subjected to the culturing operation as explained in Example 6.

The capsules thus obtained were immersed in an aqueous solution (pH 3.6, 20 mL) containing 1 mM gallium (III) ion. Number of the capsules immersed in the aqueous solution was 100. Number of the bacteria present in the capsules immersed in the aqueous solution was $3.0 \times 10^{10}$ cells/ml.

Concentrations of gallium contained in the aqueous solution were measured using an ICP light emission spectral analysis device at a time before capsule immersion, and at time of 15 minutes, 30 minutes, 1 hour, 3 hours, and 6 hours after capsule immersion. A collection rate of gallium after 6 hours from capsule immersion in Example 8 was 79.2%.

In addition, as a comparative test, the aqueous solution containing gallium ion was employed as it was without the capsules, and a gallium concentration was measured at each of the aforementioned times.

Figure 9:
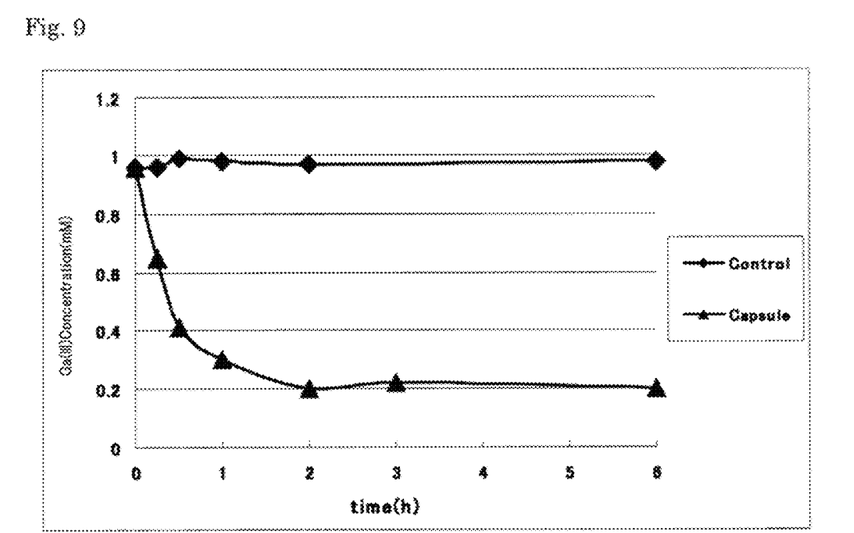
FIG. 9 is a graph chart showing changes in gallium (III) concentration in an aqueous solution in Example 8 and Comparative Test.

A graph showing changes in gallium (III) ion concentration in the aqueous solution in Example 8 and this comparative test is shown in FIG. 9.

Example 9

The capsules for collecting a non-ferrous metal having a three-layered structure immediately after manufacturing, manufactured in Example 6 were subjected to the culturing operation as explained in Example 6.

The resulting capsules were immersed in an aqueous solution (pH 7.0, 20 mL) containing 1 mM rhodium (III) ion and 50 mM sodium formate. Number of the capsules immersed, in the aqueous solution was 100. Number of the bacteria present in the capsule immersed in the aqueous solution was $3.0 \times 10^{10}$ cells/ml.

Concentrations of rhodium contained in the aqueous solution were measured using an ICP light emission spectral analysis device a time before capsule immersion, and at times of 10 minutes, 30 minutes, 1 hour, 3 hours, and 6 hours after capsule immersion. A collection rate of rhodium after 6 hours from capsule immersion in Example 9 was 58.0%.

In addition, as a comparative test, the aqueous solution was employed as it was without the capsules and a rhodium concentration was measured at each of the aforementioned times.

Figure 10:
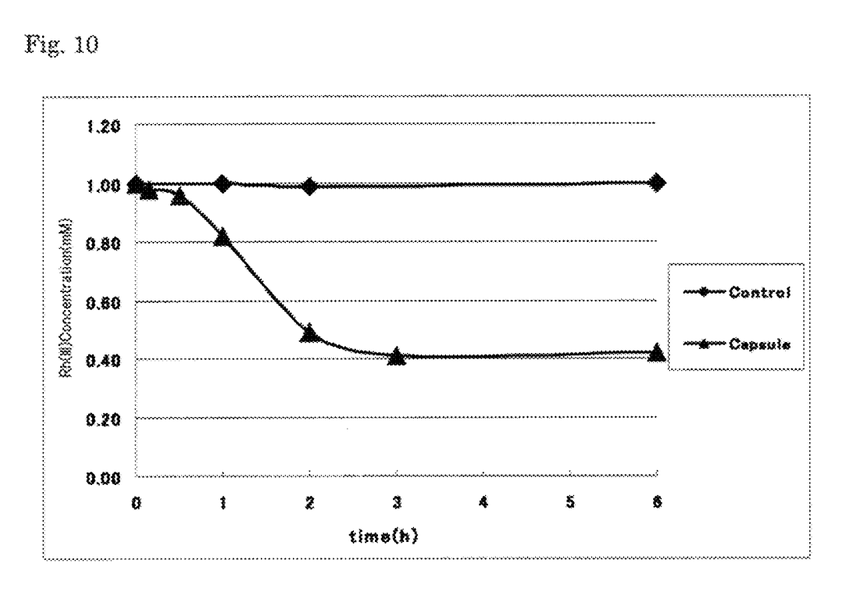
FIG. 10 is a graph chart showing changes in rhodium (III) concentration in an aqueous solution in Example 9 and Comparative Test.

A graph showing changes in rhodium (III) ion concentration in the aqueous solution in Example 9 and this comparative test is shown in FIG. 10.

Example 10

The capsules for collecting a non-ferrous metal having a three-layered structure immediately after manufacturing, manufactured in Example 6 were subjected to the culturing operation as in Example 6.

The resulting capsules were immersed in an aqueous solution (pH 5.5, 20 mL) containing 0.5 mM dysprosium (III) ion. Number of the capsules immersed in the aqueous solution was 100. Number of the bacteria present in the capsule immersed in the aqueous solution was $3.0 \times 10^{10}$ cells/ml.

Concentrations of dysprosium contained in the aqueous solution were measured using an ICP light emission spectral analysis device at a time before capsule immersion, and at times of 15 minutes, 30 minutes, 1 hour, 3 hours, and 6 hours after capsule immersion. A collection rate of rhodium after 6 hours from capsule immersion in Example 10 was 88.0%.

In addition, as a comparative test, the aqueous solution was employed without the capsules, and a dysprosium concentration was measured at each of the aforementioned times.

Figure 11:
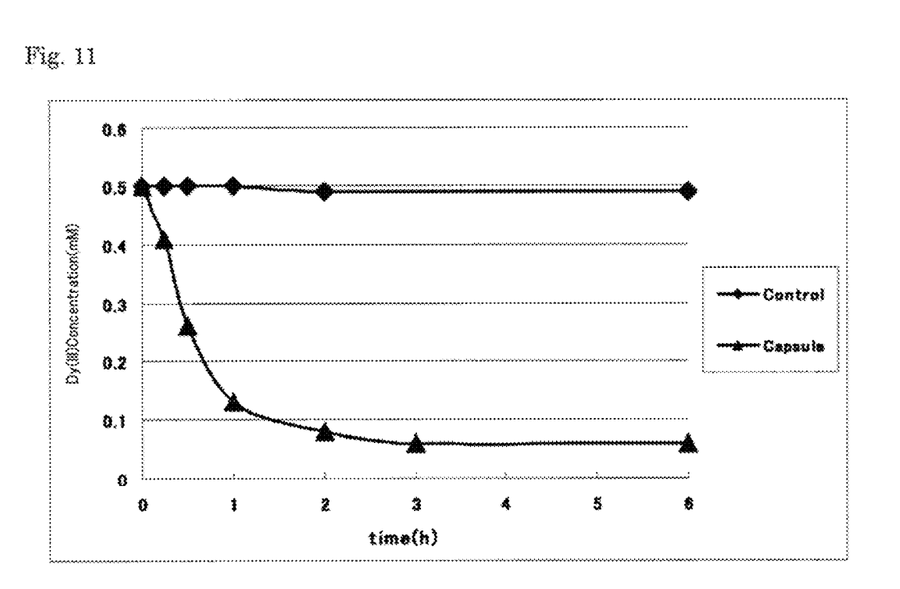
FIG. 11 is a graph chart showing changes in dysprosium (III) concentration in an aqueous solution in Example 10 and Comparative Test.

A graph showing changes in dysprosium (III) ion concentration in the aqueous solution in Example 9 and this comparative test is shown in FIG. 11.

As shown in Examples 7 to 10, it was confirmed that a variety of non-ferrous metals such as platinum, gallium, rhodium and a rare earth element could be collected using the capsules for collecting a non-ferrous metal of the present invention.

In Examples, a collection rate and/or a collection speed of a non-ferrous metal can be improved by a method, e.g. (1) an increase of number of bacteria contained in the capsule for collecting a non-ferrous metal, (2) an increase of number of capsules for collecting a non-ferrous metal to be immersed in the aqueous solution, and (3) a design change of a particle size of the capsule for collecting a non-ferrous metal to a range of 0.1 to 2 mm.

INDUSTRIAL APPLICABILITY

The capsule for collecting a non-ferrous metal of the present invention has an advantage that, by a simple operation of immersion in a solution containing a non-ferrous metal for a given time, a non-ferrous metal can be easily collected. In collection of a non-ferrous metal using the capsule for collecting a non-ferrous metal of the present invention, a non-ferrous metal can be collected without accompanying consumption of a large amount of energy like a method using a chemical reaction. There is an advantage that a large amount of waste solvent like a solvent extraction method is not accompanied, and the load on the environment is also small. Further, in the present invention, since a non-ferrous metal can be collected by a simple operation of immersing a capsule for collecting a non-ferrous metal in a solution for a given period and, thereafter, taking out the capsule by a means such as filtration, there is an advantage that implementation is simple without accompanying the large cost of facility investment.

EXPLANATION OF NUMBERS IN DRAWINGS

1: Shell,
2: Oily portion,
3: Capsule content,
4: Intermediate layer portion (oily substance),
5: Hydrophilic portion,
6: Hydrophilic portion,
10: Double nozzle,
11: Capsule content,
12: Shell formation composition,
13: Formation tube,
14: Light source,
15: Separation means,
16: Carrier fluid,
17: Driving means.

What is claimed is:

1. A method for producing a seamless capsule for collecting a non-ferrous metal, comprising:
    extruding a hydrophilic composition comprising a bacteria from a first nozzle, extruding an oily composition from a second nozzle and extruding a shell formation composition from a third nozzle simultaneously into a carrier fluid, wherein the first nozzle, the second nozzle and the third nozzle are concentrically arranged with sequentially increasing radiuses in which the first nozzle is provided at the innermost position of the concentrically arranged nozzles and the third nozzle is provided at the outermost position of the concentrically arranged nozzles,
    curing the shell formation composition with light irradiation, and
    performing a bacterium culturing treatment, or immersion in a solution containing a non-ferrous metal, to localize the oily substance,
    wherein the seamless capsule comprises a capsule content and a shell covering the capsule content, and the capsule content comprises two portions: the oily substance and an aqueous solution containing the bacteria, and
    wherein the shell formation composition comprises a photocurable component and a shell permeation aid, and the photocurable component is at least one selected from the group consisting of an acrylate-based oligomer, an unsaturated polyester-based oligomer, an polyene thiol-based oligomer, a cinnamic acid-based oligomer, an epoxy-based oligomer, a vinyl ether-based oligomer and an unsaturated polyamide-based oligomer, and
    wherein the seamless capsule is immersed in a solution containing the non-ferrous metal to collect the non-ferrous metal in the seamless capsule, and the non-ferrous metal to be collected is at least one selected from the group consisting of a rare metal and a rare noble metal.

2. The method for producing a seamless capsule for collecting a non-ferrous metal according to claim 1, wherein the bacteria is at least one selected from the group consisting of *Geobacter* bacteria, *Desulfomonas* bacteria, *Desulfuromusa* bacteria, *Pelobacter* bacteria, *Shewanella* bacteria, *Ferrimonas* bacteria, *Aeromonas* bacteria, *Sulfurospirillum* bacteria, *Wolinella* bacteria, *Desulfovibrio* bacteria, *Geothrix* bacteria, *Deferribacter* bacteria, *Geovibrio* bacteria, *Pyrobaculum* bacteria, *Thermotogae* bacteria, *Archaeoglobus* bacteria, *Pyrococcus* bacteria and *Pyrodictium* bacteria.

3. The method for producing a seamless capsule for collecting a non-ferrous metal according to claim 1, wherein the shell permeation aid is at least one selected from the group consisting of alginic acid, polyvinyl alcohol, agar, carrageenan, gellan gum, pectin, starch, a starch derivative, dextrin, cellulose and protein.

4. The method for producing a seamless capsule for collecting a non-ferrous metal according to claim 1, wherein the capsule content comprises *Shewanella oneidensis* or *Shewanella* algae.

5. The method for producing a seamless capsule for collecting a non-ferrous metal according to claim 1, wherein the non-ferrous metal to be collected is palladium, platinum, rhodium, gold, silver, indium, gallium or a rare earth element.

6. The method for producing a seamless capsule for collecting a non-ferrous metal according to claim 1, wherein the capsule content further comprises at least one selected from the group consisting of an electron donating component, an electron accepting component and a liquid culture medium.

7. The method for producing a seamless capsule for collecting a non-ferrous metal according to claim 1, wherein the oily composition comprises at least one selected the group consisting of olive oil, jojoba oil, corn oil, rapeseed oil, lard, beef tallow, whale oil, castor oil, soybean oil, rice oil, rice germ oil, coconut oil, palm oil, cacao oil, avocado oil, macadamia nut oil, squalane, mink oil, turtle oil, and corn oil and sucrose acetate isobutyrate (SAIB).

8. The method for producing a seamless capsule for collecting a non-ferrous metal according to claim 1, wherein the bacteria is *Shewanella* bacteria, and is contained at a ratio of 1 cell/capsule to $5 \times 10^{11}$ cells/capsule, based on one capsule.

* * * * *